US010843044B2

(12) United States Patent
Conan et al.

(10) Patent No.: US 10,843,044 B2
(45) Date of Patent: Nov. 24, 2020

(54) EYEGLASSES

(71) Applicant: DECATHLON, Villenueve d'Ascq (FR)

(72) Inventors: Mathieu Conan, Lille (FR); Antoine Harpages, Guethary (FR); André Weinert, Altdorf (DE); Damien Saumureau, Saint Pée sur Nivelle (FR)

(73) Assignee: DECATHLON, Villenueve d'Ascq (FR)

( * ) Notice: Subject to any disclaimer, the term of this patent is extended or adjusted under 35 U.S.C. 154(b) by 98 days.

(21) Appl. No.: 16/099,810

(22) PCT Filed: May 11, 2017

(86) PCT No.: PCT/FR2017/051126
§ 371 (c)(1),
(2) Date: Nov. 8, 2018

(87) PCT Pub. No.: WO2017/194884
PCT Pub. Date: Nov. 16, 2017

(65) Prior Publication Data
US 2019/0083849 A1 Mar. 21, 2019

(30) Foreign Application Priority Data
May 12, 2016 (FR) .................................. 16 54250

(51) Int. Cl.
G02C 5/12 (2006.01)
A63B 33/00 (2006.01)
(Continued)

(52) U.S. Cl.
CPC ............ A63B 33/002 (2013.01); A61F 9/027 (2013.01); G02C 5/122 (2013.01);
(Continued)

(58) Field of Classification Search
CPC .......... G02C 7/066; G02C 5/02; G02C 5/126; G02C 5/12
(Continued)

(56) References Cited

U.S. PATENT DOCUMENTS 6,056,398 A * 5/2000 Negishi .................. G02C 5/124
351/55

FOREIGN PATENT DOCUMENTS

CN 2401911 Y 10/2000
DE 3934163 A1 4/1991
(Continued)

OTHER PUBLICATIONS

International Search Report issued in corresponding application No. PCT/FR2017/051126, dated Jul. 10, 2017.

Primary Examiner — Hung X Dang
(74) Attorney, Agent, or Firm — Murtha Cullina LLP

(57) ABSTRACT

The invention relates to eyeglasses having two lens units that are fitted with a device for keeping the eyeglasses on a wearer's head. The eyeglasses having a nose bridge that connects the two lens units and includes a central portion to be disposed about the wearer's nose At least one of the lens units has a duct inside to which a lateral portion of the nose bridge is slidingly mounted using a mechanism for adjusting the position of the lens unit relative to the nose bridge. The adjusting mechanism has a member that is rotatably mounted in the duct. The member and the lateral portion of the nose bridge comprise a coupler designed to convert the rotation of the member into a relative translational movement between the lateral portion and the duct.

17 Claims, 4 Drawing Sheets

(51) Int. Cl.
  *A61F 9/02* (2006.01)
  *G02C 3/00* (2006.01)
  *G02C 5/04* (2006.01)
  *A63B 71/06* (2006.01)

(52) U.S. Cl.
  CPC ... *A61F 2009/021* (2013.01); *A63B 2033/008* (2013.01); *A63B 2071/0694* (2013.01); *G02C 3/003* (2013.01); *G02C 5/04* (2013.01); *G02C 5/124* (2013.01)

(58) Field of Classification Search
  USPC ........................................ 351/137, 136, 138
  See application file for complete search history.

(56) References Cited

FOREIGN PATENT DOCUMENTS

| | | |
|---|---|---|
| DE | 9005624 U1 | 9/1991 |
| EP | 0891788 A1 | 1/1999 |
| FR | 1264925 A | 6/1961 |
| GB | 2326078 A | 12/1998 |
| WO | 2011002194 A2 | 1/2011 |

* cited by examiner

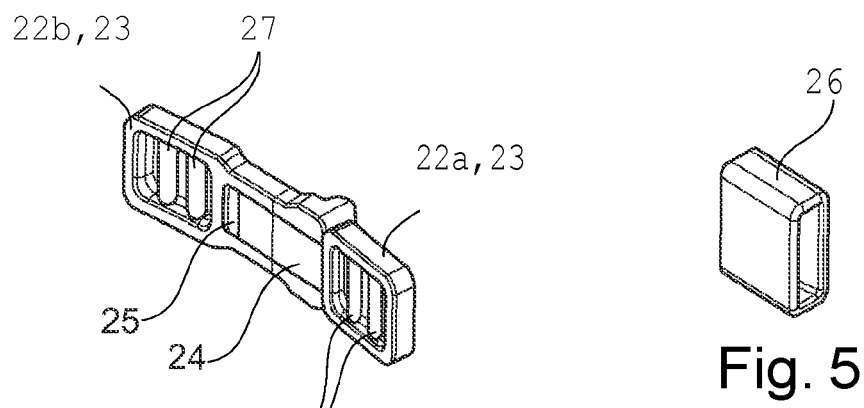
Fig. 4a
Fig. 5
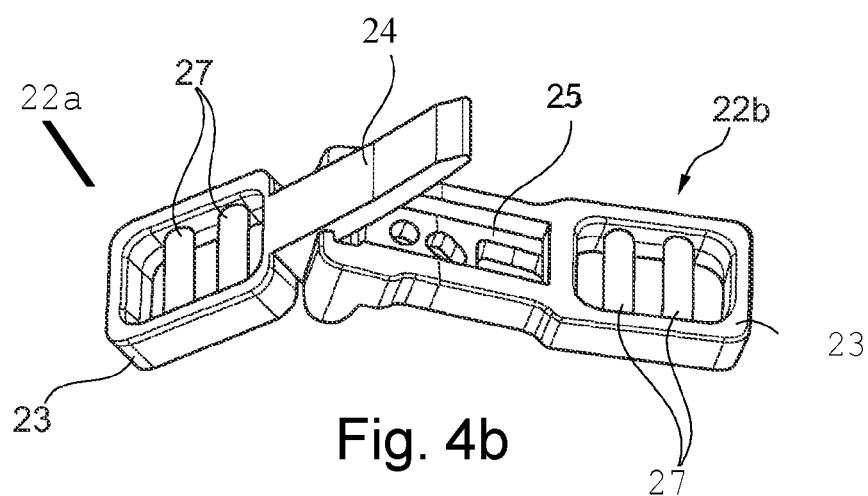
Fig. 4b
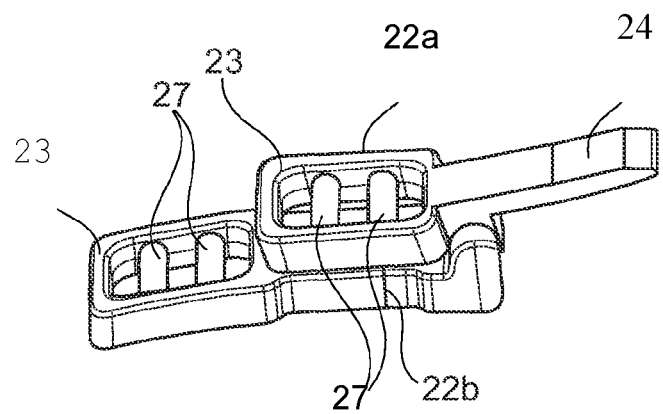
Fig. 4c

EYEGLASSES

CROSS-REFERENCE TO RELATED APPLICATION

This application claims the benefit of International application number PCT/FR2017/051126, filed May 11, 2017 and French patent application number 1654250, filed on May 12, 2016, the entire contents of which are incorporated herein by reference

TECHNICAL FIELD

The invention relates to eyeglasses comprising two lens units, each of which is provided with a transparent wall through which viewing occurs, said lens units further being equipped with a retaining device for keeping said eyeglasses on a wearer's head.

BACKGROUND

It applies in particular to eyeglasses intended for practising water sports activities such as swimming. In such a case, the rear periphery of each lens unit can be equipped with a seal intended to mould to the wearer's face, in order to prevent water from penetrating between said lens unit and the eye of said wearer.

Moreover, the retaining device for keeping the eyeglasses on the wearer's head can comprise at least one flexible strap, in particular made of an elastic material, the ends whereof are attached to a means, for example an adjustment slot or buckle, associated with an outer edge of respectively one lens unit.

Conventionally, the lens units are connected to one another by a nose bridge, which has a central portion intended to be positioned about the wearer's nose, as well as two lateral portions, each of which is secured to an inner edge of respectively one of said units.

In some versions, the positioning of the lens units relative to the nose bridge is adjustable, so as to be capable of adjusting the eyeglasses to suit the morphology of the wearer's face, and thus improve wearing comfort, or, in the case of eyeglasses adapted to suit the practice of water sports activities, to guarantee a good seal between said eyeglasses and said face.

For this purpose, eyeglasses are known in which each of the lens units has an inner edge equipped with a slot through which a lateral portion of the nose bridge is mounted, said lateral portion having notches that are distributed over a portion of the length thereof and which are intended to be selectively engaged in said slot, according to the desired position of each of the lens units.

However, this solution is not entirely satisfactory, in that it requires forcefully passing the notches into the slots, which can damage the nose bridge in the long term, and thus reduce the lifetime of the eyeglasses. Moreover, in order to reduce the bulkiness of the nose bridge, the lateral portions generally have three notches at most, which limits the adjustment possibilities.

In order to overcome these drawbacks, solutions have been proposed in which at least one of the lens units has an inner edge equipped with a duct in which a lateral portion of the nose bridge is mounted such that it slides via a device for adjusting the positioning of said lens unit relative to said nose bridge.

Thus, eyeglasses are known from document CN-2 401 911 in which the nose bridge has two threads formed on each of the lateral portions thereof, each of said lateral portions being capable of being screwed into a tapping formed in the duct of an inner edge to allow the expected adjustment to be carried out.

Moreover, document EP-0 891 788 discloses eyeglasses in which inserts are arranged in each of the lateral portions in order to locally increase the diameter thereof, such that it is greater than the inner diameter of the duct of the inner edge, while allowing said lateral portion to slide relative to said insert by manual traction.

However, these solutions are also not entirely satisfactory, in that the adjustment that they propose remains relatively imprecise and lacks ergonomics.

SUMMARY OF THE INVENTION

The invention aims to perfect the prior art, in particular by proposing eyeglasses in which the positioning of at least one lens unit relative to the nose bridge can be adjusted in a very precise manner using a device that is simple, long-lasting and ergonomic to use.

For this purpose, the invention relates to eyeglasses comprising two lens units that are equipped with a retaining device for keeping said eyeglasses on a wearer's head, as well as a nose bridge that connects said units while having a central portion intended to be positioned about the wearer's nose, at least one of said units being equipped with a duct inside which a lateral portion of the nose bridge is mounted such that it slides by means of a device for adjusting the positioning of said lens unit relative to said nose bridge, the adjusting device comprising a member that is rotatably mounted in the duct, said member and the lateral portion of the nose bridge comprising coupling means that are designed to convert the rotation of said member into a relative translational movement between said lateral portion and said duct.

BRIEF DESCRIPTION OF THE DRAWINGS

Other features and advantages of the invention can be clearly observed in the following description, which is given with reference to the accompanying figures, in which:

FIGS. 4a, 4b and 4c are partial, perspective representations of the fasteners intended to secure the free ends of two flexible straps together to form a retaining device for keeping the eyeglasses according to FIG. 1 on the wearer's head, respectively with the actuating member in the stowed position (FIG. 4a), during the displacement of said member to the position of use thereof (FIG. 4b) and with said member in the position of use (FIG. 4c);

FIG. 5 is a perspective representation of a means designed to ensure the reversible locking of the fasteners in FIG. 4 in the stowed position of the tool.

DETAILED DESCRIPTION

Figure 1A:
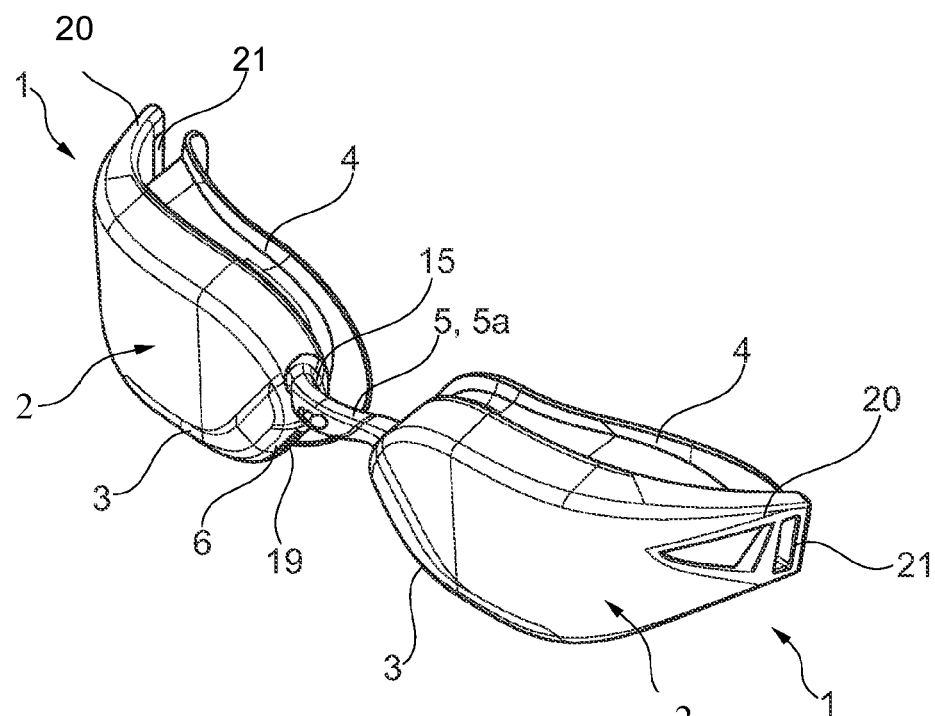
FIGS. 1a, 1b, 1c and 1d are partial representations of eyeglasses according to one embodiment of the invention, respectively from a perspective overhead view (FIG. 1a), from a perspective bottom view (FIG. 1b), from a front view (FIG. 1c) and from a bottom view (FIG. 1d)
Figure 1B:
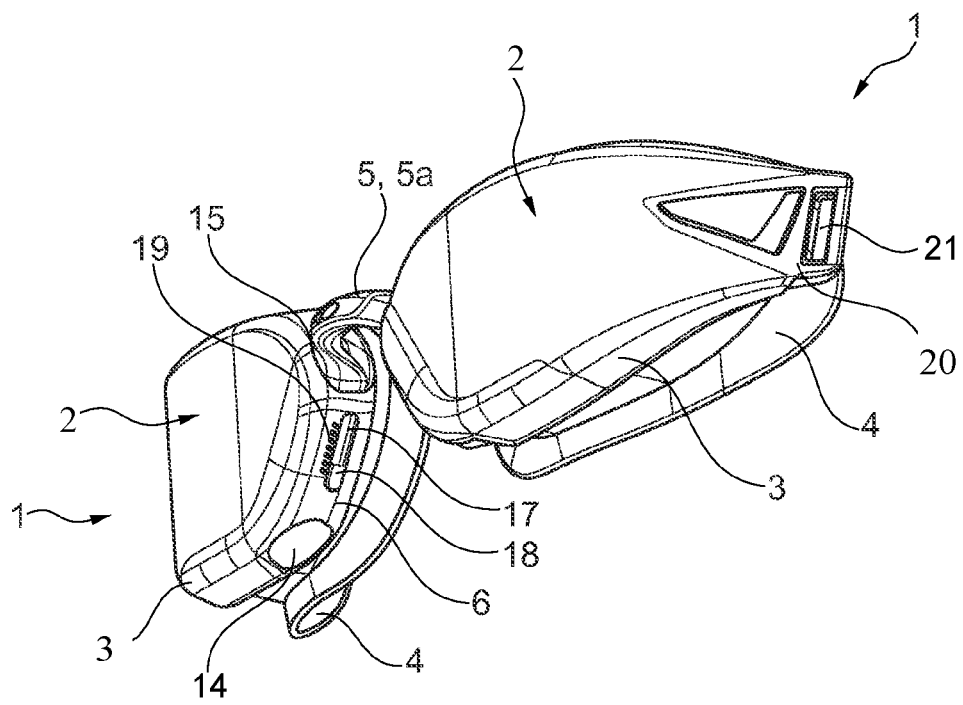
Figure 1C:
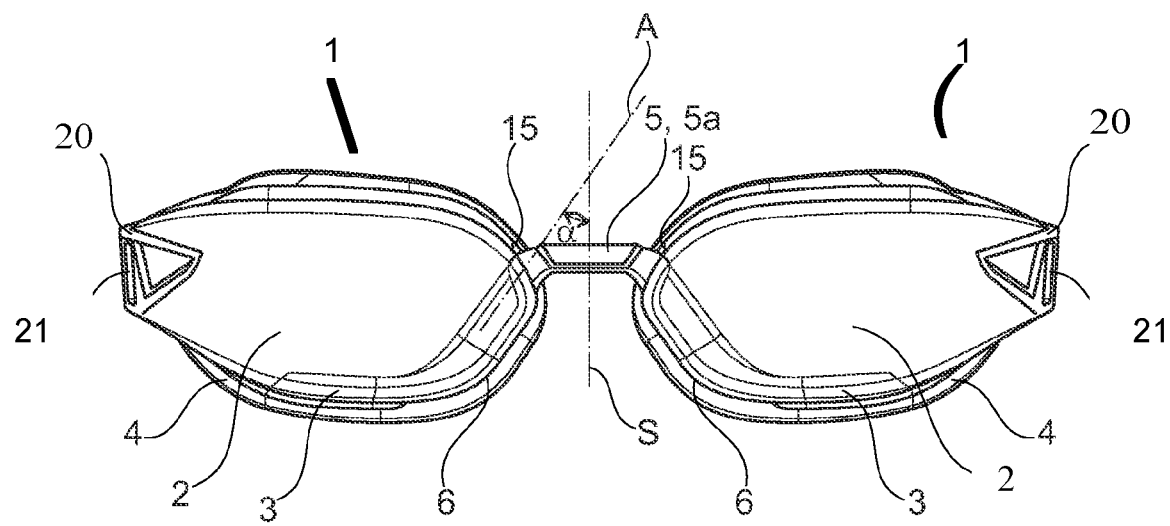
Figure 1D:
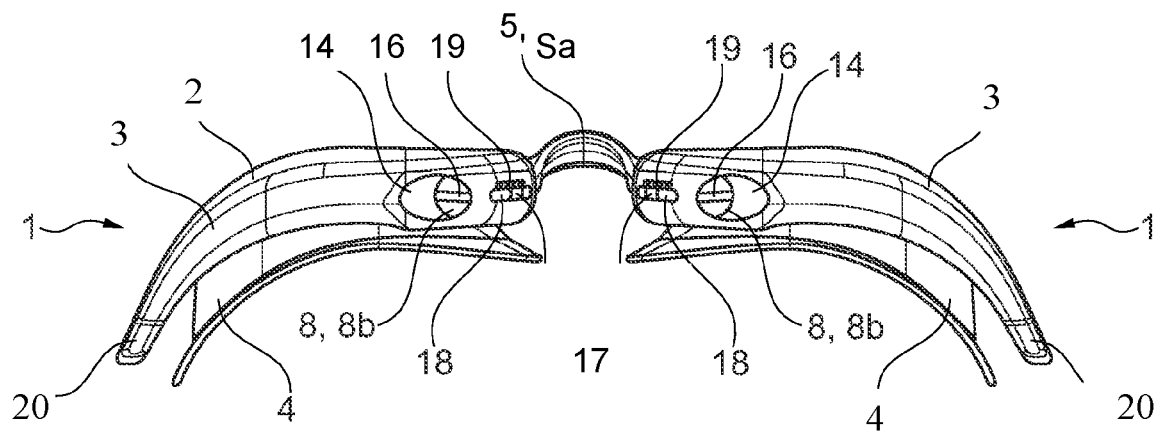
Figure 2:
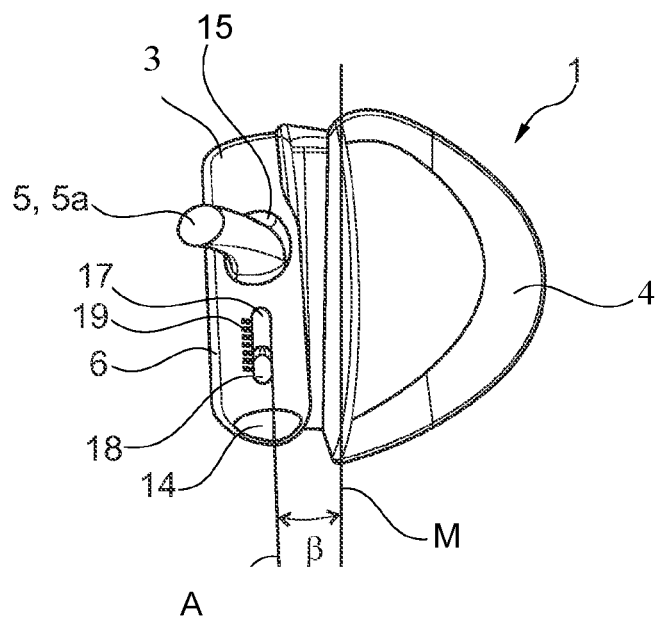
FIG. 2 is a partial representation from an inner side view of a lens unit of the eyeglasses according to FIG. 1, a longitudinal section whereof has been made at the level of the nose bridge.
Figure 3:
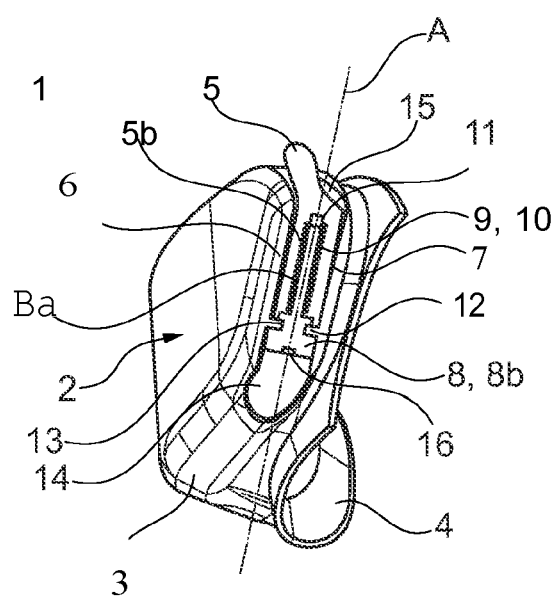
FIG. 3 is a partial, perspective representation of a lens unit of the eyeglasses according to FIG. 1, a longitudinal section whereof has been made at the level of the duct in order to show the coupling of the member and of the lateral portion of the nose bridge.

In this description, the spatial positioning terms are given with reference to the position of the eyeglasses relative to the face of a wearer having put on the eyeglasses. In particular, the terms "rear" and "front" are given relative to an arrangement that is respectively facing the face and opposite the face, and the terms "inner" and "outer" are given relative to arrangements that are respectively close and distant from the wearer's nose. Moreover, the terms "axial" and "radial" are given with reference to the longitudinal axis A of a duct as shown in FIGS. 1c, 2 and 3, and correspond to a direction that is respectively parallel and perpendicular to this axis A.

With reference to these figures, the description below describes eyeglasses that are in particular intended to be used while practising water sports activities such as swimming.

The eyeglasses comprise two lens units 1, each of which has a transparent wall 2 arranged such that viewing takes place therethrough when the eyeglasses are worn by the wearer, for example by being made of glass or of a transparent thermoplastic polymer material. In particular, the optical properties of the transparent wall 2 can be designed to adapt to the wearer's view and/or to the ambient brightness.

In the embodiment shown, each lens unit 1 has a shroud 3 that at least partially encircles the transparent wall 2, in particular in order to provide peripheral protection to the transparent wall and/or to improve the aesthetic appearance of the eyeglasses. The shrouds 3 can be made of a rigid material, for example having a thermoplastic polymer base, in particular made in one piece with the transparent wall 2.

Moreover, the transparent wall 2 of each lens unit 1 has a rear periphery that is equipped with a seal 4 intended to mould to the wearer's face, in particular in order to prevent water from penetrating between the wearer's eye and the transparent wall. In particular, the seal 4 can be made of a flexible elastomeric material and arranged so as to bear, in a peripheral, water-tight manner, about the wearer's eye.

The eyeglasses further comprise a nose bridge 5 that connects the lens units, the nose bridge having a central portion 5a intended to be arranged about the nose of a wearer when wearing the eyeglasses, as well as two lateral portions 5b that extend on either side of the central portion and that are each associated with an inner edge 6 of respectively one lens unit 1.

According to one embodiment, the nose bridge 5 is U-shaped, the central portion 5a and the lateral portions 5b of the nose bridge being formed by the elbow and by each of the branches of the U shape respectively.

In particular, the nose bridge 5 is arranged so as to be able to correctly position the lens units 1 over the eyes of the wearer, either by having at least one central portion 5a made of a flexible material, for example having an elastomeric polymer base, in order to allow, through the deformable nature thereof, good adaptation to the morphology of the face of the wearer, or by being made of a rigid material with the possibility of adjusting the positioning of at least one unit 1 relative to the nose bridge 5.

For this purpose, at least one of the lens units 1 is equipped with a duct 7 in which a lateral portion 5b of the nose bridge 5 is mounted such that it slides, in particular along the longitudinal axis A of the duct, this being carried out via a device for adjusting the positioning of the lens unit relative to the nose bridge.

In the embodiment shown, such a duct 7 is formed on the inner edge 6 of the shroud 3 of each of the lens units. Alternatively, the duct 7 can be formed on another portion of the shroud 3, for example on the upper or lower edge thereof.

The nose bridge 5 has two lateral portions 5b that are mounted such that they slide in respectively one of the ducts 7 by means of an adjusting device. Thus, it is possible to adjust the relative positioning of the lens units 1 on the nose bridge 5, i.e. the separation distance therebetween, in particular in the case of a rigid nose bridge 5, but also the positioning thereof relative to one another. Alternatively, only the lateral portions 5b of the nose bridge 5 are rigid, whereby the central portion 5a is flexible such that the adjustment can stress the deformation distance between the lens units 1.

In particular, with reference to FIG. 1c, the longitudinal axis A of each duct 7 can form an angle $\alpha$ that lies in the range from 30° to 60°, in particular less than 45° and for example about 34°, with a vertical plane S of symmetry of the eyeglasses. Thus, the positioning of the lens units 1 between one another and relative to the face is substantially preserved during adjustment, while increasing or decreasing the separation distance therebetween.

Moreover, the longitudinal axis A of each duct 7 can form an angle $\beta$ that lies in the range from 1° to 10°, in particular about 5°, with a median plane M of the lens unit 1 that is substantially parallel to the wearer's face. Thus, when distancing the lens units 1 from one another, the lens units 1 move slightly forward or backward depending on the adjustment direction to improve the adaptation of the eyeglasses to the morphology of the wearer's face.

The adjusting device comprises a member 8 mounted such that it rotates in the duct 7, in particular about the axis A, the member and the lateral portion 5b of the nose bridge 5 comprising coupling means that are designed to convert the rotation of the member into a relative translational movement between the lateral portion and the duct.

In particular, the coupling means can comprise a thread 9 and a tapping 10 formed on respectively one of either the member 8 and the lateral portion 5b of the nose bridge 5. With reference to FIG. 3, the member 8 comprises a rod 8a, the periphery whereof is provided with a thread 9, the lateral portion 5b comprising a bore 11 in which the rod is arranged and which is provided with a tapping 10 complementing the thread.

The member 8 further comprises an actuating head 8b for actuating the rotation thereof in the duct 7, the head being formed on the proximal end of the rod 8a. Furthermore, the duct 7 has an inner flange 12 through which the member 8 is engaged, the member having a groove 13 formed between the actuating head 8b and the proximal end of the rod 8a, and in which the flange is arranged in axial interference.

Thus, the translational movement of the member 8 in the duct 7 is blocked and, since the rotational movement of the lateral portion 5b in the duct is blocked, the rotation of the member 8 results in a relative translational movement between the lateral portion and the duct in order to obtain the expected adjustment.

In the embodiment shown, the duct 7 has a lower opening 14 through which the actuating head 8b can be accessed, as well as an upper opening 15 from which the central portion 5a of the nose bridge 5 extends.

Moreover, the actuating head 8b comprises a recess 16 designed to allow the member 8 to be rotatably actuated by means of a tool, for example in the form of a screwdriver.

Thus, by using this device, the wearer can very precisely adjust the positioning of the lens units 1, which allows him/her to optimally adapt the eyeglasses to suit his/her morphology. Furthermore, the adjustment can be carried out in a particularly simple and intuitive manner, in that the actuation of the member 8 allows for direct adjustment, without the need for additional handling operations, in particular of the nose bridge 5, and without causing the nose bridge to rotate.

The duct 7 has a slot 17 that opens out laterally, the lateral portion 5b having a slider 18 that is arranged inside the slot. In particular, the slider 18 acts as a travel limit stop for the displacement of the lateral portion 5b in the duct 7, so that the portion cannot leave the duct and thus remains coupled to the member 8.

In order to improve adjustment precision, the device can comprise a means for viewing the position of the lateral portion 5b in the duct 7. In the embodiment shown, the eyeglasses comprise graduations 19 that are arranged along the slot 17 so as to quantify the position of the lateral portion 5b in the duct 7, according to the relative position of the slider 18 relative to the graduations, which allows the wearer to more easily and more quickly make an adjustment to suit his/her morphology, in particular between two uses of the eyeglasses.

In order to ensure that the eyeglasses remain on a wearer's head, the lens units 1 are equipped with a device designed for this purpose. To achieve this, with reference to the figures, each lens unit 1 comprises an outer edge 20 equipped with a means, in particular a cavity 21, for the attachment of such a device.

In the embodiment shown, the cavity 21 is formed on the outer edge 20 of the shroud 3 of each lens unit 1. Alternatively, in particular for lens units 1 devoid of a shroud, the cavity 21 can be formed directly on the outer edge of the transparent wall 2.

In particular, specifically for eyeglasses intended for practising water sports activities, the retaining device for keeping the eyeglasses on the wearer's head can comprise at least one flexible strap, for example made of an elastic material, the length whereof can be adjusted to suit the size of the wearer's head.

With reference to FIGS. 4a-4c and 5, the retaining device comprises two straps (not shown), each of which has a free end that is equipped with a fastener 22a, 22b for fastening to the other strap, each of the fasteners comprising a rigid buckle 23 in which one of the free ends slides in order to allow the length of the corresponding strap to be adjusted.

Each of the buckles 23 has two supports 27 about which the free end of a strap selectively passes, on the one hand in order to adjust the length of the strap by sliding the end in one direction and, on the other hand, in order to prevent the length from loosening by preventing the end from sliding in the opposite direction.

Advantageously, the retaining device incorporates a tool 24 for actuating the rotational movement of the member 8 in the duct 7. Thus, the wearer has such a tool 24 at his/her disposal at all times when using the eyeglasses, such that he/she can adjust the set length of the central portion 5a at any time, without the risk of losing the tool 24 between two uses.

For this purpose, the device can comprise at least one strap equipped with a fastener 22a that carries such a tool 24, the tool being capable of being deployed, in particular from the fastener, to allow for the use thereof.

With reference to FIGS. 4a-4c and 5, the fasteners 22a, 22b of each of the retaining straps respectively carry the tool 24 and a housing 25, in particular having a shape that complements that of the tool, the fasteners being secured to one another so as to allow the tool to be displaced between a deployed position of use (FIG. 4c) and a stowed position inside the housing 25 (FIG. 4a).

In the embodiment shown, the tool 24 is mounted such that it rotates on the other fastener 22b between the deployed and stowed positions thereof, which allows for the simple and fast passage from one position to the other.

In particular, the fasteners 22a, 22b are secured to one another in rotation, at the level of the rotational axis of the tool 24 between the deployed and stowed positions thereof, which allows the adjusted length of the straps to be preserved, regardless of the position of the tool.

Moreover, the fasteners 22a, 22b comprise a means for locking the fasteners in the stowed position of the tool 24, for example the tool 24 can be clipped inside the housing 25 in the stowed position. Furthermore, a keeper 26 is mounted such that it slides between the two buckles 23 to guarantee, depending on the position thereof relative to the buckles, the locking or to release the displacement of the tool between the two positions thereof (FIG. 5).

What is claimed is:

1. Eyeglasses comprising two lens units that are equipped with a retaining device for keeping the eyeglasses on a wearer's head, as well as a nose bridge that connects the units while having a central portion intended to be positioned about the wearer's nose, at least one of the units being equipped with a duct inside which a lateral portion of the nose bridge is mounted to an adjusting device for positioning of the lens unit relative to the nose bridge, the eyeglasses wherein the adjusting device comprises a member that is rotatably mounted in the duct, the member and the lateral portion of the nose bridge comprising a coupler adapted to convert the rotation of the member into a relative translational movement between the lateral portion and the duct.

2. The eyeglasses according to claim 1 wherein the coupler comprises a thread and a tapping formed on respectively one of either the member and the lateral portion of the nose bridge.

3. The eyeglasses according to claim 1, wherein the member comprises an actuating head for actuating the rotation thereof in the duct.

4. The eyeglasses according to claim 3, wherein the duct has a lower opening through which the actuating head can be accessed, as well as an upper opening from which the central portion of the nose bridge extends.

5. The eyeglasses according to claim 3, wherein the actuating head comprises a recess adapted to allow the member to be rotatably actuated by a tool.

6. The eyeglasses according to claim 1, wherein the adjusting device comprises a means for viewing the position of the lateral portion in the duct.

7. The eyeglasses according to claim 1, wherein the duct has a slot that opens out laterally, the lateral portion having a slider that is arranged inside the slot.

8. The eyeglasses according to claim 1, wherein the translational movement of the member in the duct is blocked, and the rotational movement of the lateral portion in the duct is blocked.

9. The eyeglasses according to claim 1, wherein the retaining device incorporates a tool for actuating the rotational movement of the member in the duct.

10. The eyeglasses according to claim 9, wherein the retaining device comprises at least one strap equipped with a fastener that carries the tool that is capable of being deployed to allow for the use thereof.

11. The eyeglasses according to claim 10, wherein the retaining device comprises two straps, each of which is equipped with a fastener that carries the tool and a housing respectively, the fasteners being secured to one another so as to allow the tool to be displaced between a deployed position of use and a stowed position inside the housing.

12. The eyeglasses according to claim 11, wherein the fasteners are secured to one another in rotation, at the level of a rotational axis of the tool between the deployed and stowed positions thereof.

13. The eyeglasses according to claim 11, wherein each of the fasteners comprises a rigid buckle in which a free end of a strap slides in order to allow the length of the strap to be adjusted.

14. The eyeglasses according to claim 1, wherein each lens unit comprises a transparent wall, the rear periphery whereof is equipped with a seal intended to mould to the wearer's face.

15. The eyeglasses according to claim 1, wherein each lens unit has an inner edge equipped with a duct in which a lateral portion of the nose bridge is mounted such that it slides via an adjusting device so as to be able to adjust the relative positioning of the units on the nose bridge.

16. The eyeglasses according to claim 1, wherein the duct is formed on an inner edge of a lens unit, the duct having a longitudinal axis (A) forming an angle $\alpha$ that lies in the range from 30° to 60° with a vertical plane (S) of symmetry of the eyeglasses.

17. The eyeglasses according to claim 16, wherein the longitudinal axis (A) of the duct forms an angle $\beta$ that lies in the range from 1° to 10° with a median plane (M) of the lens unit.

\* \* \* \* \*